US008452610B2

(12) United States Patent
Lipner et al.

(10) Patent No.: US 8,452,610 B2
(45) Date of Patent: May 28, 2013

(54) METHOD AND SYSTEM FOR DETERMINING A FAIR BENCHMARK FOR PHYSICIANS' QUALITY OF PATIENT CARE

(75) Inventors: Rebecca S. Lipner, Wayne, PA (US); Brian J. Hess, Flourtown, PA (US); Weifeng Weng, Wynnewood, PA (US); Gerald K. Arnold, Philadelphia, PA (US)

(73) Assignee: American Board of Internal Medicine, Philadelphia, PA (US)

( * ) Notice: Subject to any disclaimer, the term of this patent is extended or adjusted under 35 U.S.C. 154(b) by 262 days.

(21) Appl. No.: 12/619,333

(22) Filed: Nov. 16, 2009

(65) Prior Publication Data
US 2011/0119072 A1    May 19, 2011

(51) Int. Cl.
*G06Q 50/00*    (2012.01)
(52) U.S. Cl.
USPC .................................................. 705/2; 705/3
(58) Field of Classification Search
USPC ......................................................... 705/2, 3
See application file for complete search history.

(56) References Cited

U.S. PATENT DOCUMENTS

| 5,652,842 | A * | 7/1997 | Siegrist et al. ..................... 705/2 |
| 2004/0267570 | A1 | 12/2004 | Becker | |
| 2008/0133290 | A1* | 6/2008 | Siegrist et al. ..................... 705/7 |
| 2009/0228330 | A1 | 9/2009 | Karras et al. | |

OTHER PUBLICATIONS

J. Boulet, A. De Champlain & D. McKinley, Setting Defensible Performance Standards on OSCE's and standardized patient examinations, Medical Teacher, vol. 24, No. 3, May 2003, pp. 245-249, [online] [retrieved on Jan. 6, 2011, 246, abstract and col. 1-2 Retrieved from the Internet <http://medicina.udd.cl/ode/files/2010/07/Boulet_2045.pdf>.
International Search Report and Written Opinion for International Application No. PCT/US2010/56781 (mailed Jan. 14, 2011).
Angoff, William E. "Scales, Norms, and Equivalent Scores." In R. L. Thorndike (Ed.), Educational Measurement (2nd ed). Washington, DC: American Council on Education; pp. 508-600 (1971).
Boulet, J.R. et al. "Setting defensible performance standards on OSCEs and standardized patient examinations." *Med Tech* 25(3):245-249 (2003).
Landon, B.E. et al. "Physician Clinical Performance Assessment: Prospects and Barriers" *JAMA* 290(9):1183-1189 (2003).
McKinley, D.W. et al. "A Work-centered approach for setting passing scores on performance-based assessments." *Eval. Health Prof.* 28(3):349-369 (2005).
Mosier, C.I. "On the reliability of a weighted composite." *Psychometrika* 8(3):161-168 (1943).
Reeves, D. et al. "Combining multiple indicators of clinical quality: An evaluation of different analytic approaches." *Med Care* 45(6):489-496 (2007).

* cited by examiner

*Primary Examiner* — Lena Najarian
(74) *Attorney, Agent, or Firm* — Ballard Spahr LLP

(57) ABSTRACT

Described herein are systems, methods and computer-program products for application of both the Angoff standard-setting procedure with the Dunn-Rankin scaling method to determine standards (or cutscores) for practice-based performance assessments. In addition, reliability of measures and overall performance scores, and estimates of the decision consistency of the resulting performance standard can be calculated.

28 Claims, 27 Drawing Sheets

| Measure | Performance Level |
|---|---|
| Process Measures | |
| Ophthalmologic Examination | Completed |
| Nephropathy Assessment | Completed |
| Podiatry Examination | Completed |
| Smoking Status & Cessation Advice / Treatment | Completed |
| Intermediate Outcome Measures | |
| HgBA$_{1c}$ Poor Control | > 9.0% |
| HgBA$_{1c}$ at Goal | < 8.0% or < 7.0% (based on the patient) |
| Blood Pressure Poor Control | >= 140/90 |
| Blood Pressure Superior Control | < 130/80 |
| LDL Poor Control | >= 130 mg/dl |
| LDL Superior Control | < 100 mg/dl |
| Patient Experience Measures | |
| Overall Diabetes Care Satisfaction (1 survey question) | Excellent or very good responses |
| Patient Self-care Support (7 survey questions combined) | Excellent or very good responses |

FIG. 1

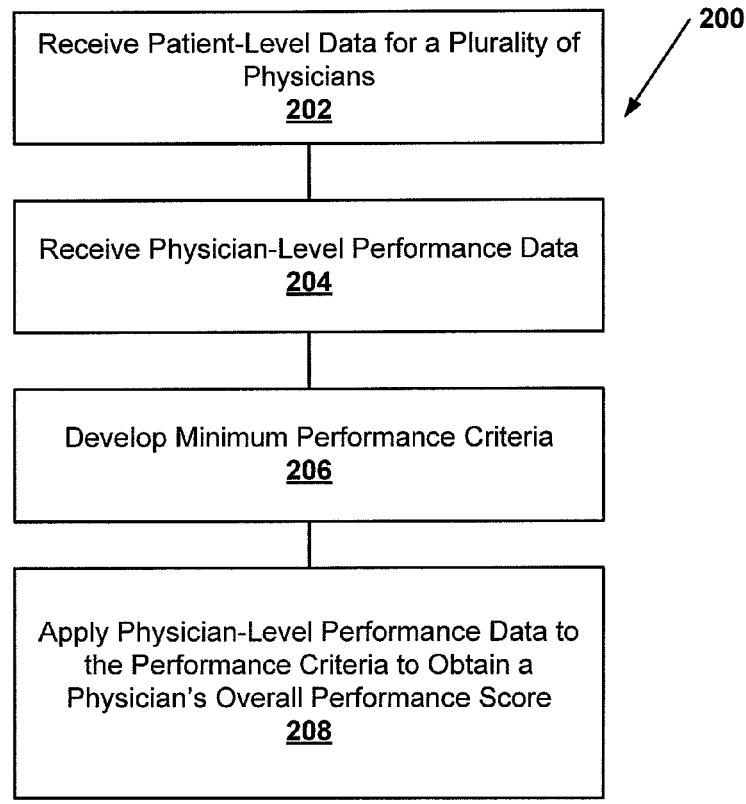

FIG. 2A

|                                          | Patient level | | Clustered at physician level | |
|------------------------------------------|------|------|--------------|-------------|
| Characteristic                           | Mean | SD   | Mean (SD)    | Range       |
| Age                                      | 59   | 11   | 59 (3.7)     | 46 to 67    |
| Patients with age ≥ 65                   | 37%  | 0.48 | 37% (0.14)   | 0% to 80%   |
| Male                                     | 45%  | 0.50 | 45% (0.14)   | 0% to 83%   |
| Having psychiatric/cognitive impairment  | 14%  | 0.34 | 13% (0.15)   | 0% to 67%   |
| Having problems with adherence           | 6%   | 0.24 | 6% (0.09)    | 0% to 63%   |
| Having social factors limiting self-care | 12%  | 0.33 | 12% (0.18)   | 0% to 100%  |
| Non-Hispanic White                       | 36%  | 0.48 | 35% (0.31)   | 0% to 100%  |
| Non-Hispanic Black                       | 12%  | 0.32 | 10% (0.18)   | 0% to 98%   |
| Hispanic                                 | 9%   | 0.29 | 9% (0.19)    | 0% to 100%  |
| Unknown race                             | 44%  | 0.50 | 46% (0.37)   | 0% to 100%  |
| Drug/alcohol abuse                       | 2%   | 0.16 | 2% (0.03)    | 0% to 18%   |
| Charlson Co-morbidity Index*             | 1.09 | 1.52 | 1.078 (0.54) | 0 to 2.78   |
| Patients with Charlson Co-morbidity >2   | 11%  | 0.31 | 11% (0.09)   | 0% to 44%   |

\* The Charlson Index is the most common index used to control for comorbidity in health outcomes study. The original Charlson index was developed for use with medical records and consisted of 19 different diseases weighted according to disease severity as 1, 2, 3, or 6.

FIG. 3

| Measure | Definition | Initial Angoff Estimate | Final Angoff Estimate |
|---|---|---|---|
| Process Measures | | | |
| Ophthalmologic Examination | Completed | | |
| Nephropathy Assessment | Completed | | |
| Podiatry Examination | Completed | | |
| Smoking Status and Cessation Advice and Treatment | Completed | | |
| Intermediate Outcome Measures | | | |
| HgBA1c Poor Control | > 9.0 | | |
| HgBA1c Superior Control | < 7.0 | | |
| Blood Pressure Poor Control | ≥ 140/90 | | |
| Blood Pressure Superior Control | < 130/80 | | |
| LDL Poor Control | ≥ 130 mg/dl | | |
| LDL Superior Control | < 100 mg/dl | | |
| Patient Experience Measures | | | |
| Overall Diabetes Care Satisfaction | Very good/excellent | | |
| Patient Self-care Support | Very good/excellent | | |

FIG. 4

Diabetes Care Standard-Setting Ratings

| Measure | Rater 1 | Rater 2 | Rater 3 | Rater 4 | Rater 5 | Rater 6 | Rater 7 | Rater 8 | Avg |
|---|---|---|---|---|---|---|---|---|---|
| Ophthalmologic Exam | 30 | 25 | 40 | 20 | 20 | 35 | 20 | 40 | 28.75 |
| Nephropathy Assessment | 80 | 75 | 75 | 70 | 50 | 90 | 75 | 70 | 73.13 |
| Podiatry Exam | 40 | 20 | 40 | 25 | 20 | 55 | 25 | 60 | 35.63 |
| Smoking Status and Cessation Advice/Treatment | 75 | 75 | 75 | 75 | 20 | 75 | 70 | 75 | 67.5 |
| HgBA1c Poor Control | 30 | 35 | 25 | 30 | 30 | 25 | 25 | 20 | 27.5 |
| HgBA1c At Goal | 36 | 36 | 36 | 36 | 36 | 36 | 36 | 36 | 36 |
| Blood Pressure Poor Control | 30 | 40 | 35 | 55 | 70 | 50 | 50 | 40 | 46.25 |
| Blood Pressure Superior Control | 15 | 10 | 15 | 15 | 10 | 20 | 20 | 30 | 16.88 |
| LDL Poor Control | 35 | 40 | 25 | 55 | 50 | 40 | 45 | 40 | 41.25 |
| LDL Superior Control | 25 | 20 | 20 | 25 | 20 | 30 | 20 | 30 | 23.75 |
| Overall Diabetes Care Satisfaction | 50 | 50 | 50 | 50 | 20 | 50 | 50 | 50 | 46.25 |
| Patient Self-care Support | 50 | 60 | 65 | 60 | 30 | 50 | 60 | 50 | 53.13 |

FIG. 6

Using the scale provided, circle the number to rate each of performance measures in terms of its importance for assessing how well a physician delivers competent medical care to diabetic patients.

| Not at all Important | | | | Somewhat important/ Somewhat not important | | | | | Very Important |
|---|---|---|---|---|---|---|---|---|---|
| 0 | 1 | 2 | 3 | 4 | 5 | 6 | 7 | 8 | 9 | 10 |

| Measure | Importance | | | | | | | | | | |
|---|---|---|---|---|---|---|---|---|---|---|---|
| Ophthalmologic Exam | 0 | 1 | 2 | 3 | 4 | 5 | 6 | 7 | 8 | 9 | 10 |
| Nephropathy Assessment | 0 | 1 | 2 | 3 | 4 | 5 | 6 | 7 | 8 | 9 | 10 |
| Podiatry Exam | 0 | 1 | 2 | 3 | 4 | 5 | 6 | 7 | 8 | 9 | 10 |
| Smoking Status & Cessation Advice/Treatment | 0 | 1 | 2 | 3 | 4 | 5 | 6 | 7 | 8 | 9 | 10 |
| Minimizing HgbA1c Poor Control (≥ 9.0) | 0 | 1 | 2 | 3 | 4 | 5 | 6 | 7 | 8 | 9 | 10 |
| HgBA1c Superior Control (< 7.0) | 0 | 1 | 2 | 3 | 4 | 5 | 6 | 7 | 8 | 9 | 10 |
| Minimizing Blood Pressure Poor Control (≥ 140/90 mm/Hg) | 0 | 1 | 2 | 3 | 4 | 5 | 6 | 7 | 8 | 9 | 10 |
| Blood Pressure Superior Control (< 130/80 mm/Hg) | 0 | 1 | 2 | 3 | 4 | 5 | 6 | 7 | 8 | 9 | 10 |
| Minimizing LDL Poor Control (≥ 130 mg/dl) | 0 | 1 | 2 | 3 | 4 | 5 | 6 | 7 | 8 | 9 | 10 |
| LDL Superior Control (< 100 mg/dl) | 0 | 1 | 2 | 3 | 4 | 5 | 6 | 7 | 8 | 9 | 10 |
| Overall Diabetes Care Satisfaction | 0 | 1 | 2 | 3 | 4 | 5 | 6 | 7 | 8 | 9 | 10 |
| Patient Self-care Support | 0 | 1 | 2 | 3 | 4 | 5 | 6 | 7 | 8 | 9 | 10 |

*Note.* The order of measures presented should be in random order (or counter-balanced) for each individual rater to control for the effect of presentation order.

FIG. 7

Diabetes Care: Dunn-Rankin Variance Stable Rank Sum Ratings

| Measure | Rater 1 | Rater 2 | Rater 3 | Rater 4 | Rater 5 | Rater 6 | Rater 7 | Rater 8 | Sum | mean | points |
|---|---|---|---|---|---|---|---|---|---|---|---|
| Ophthalmologic Exam | 5 | 5 | 8 | 4 | 6 | 10 | 5 | 10 | 53 | 6.625 | 8 |
| Nephropathy Assessment | 5 | 6 | 9 | 6 | 7 | 10 | 8 | 10 | 61 | 7.625 | 9 |
| Podiatry Exam | 1 | 3 | 5 | 2 | 3 | 3 | 2 | 8 | 27 | 3.375 | 4 |
| Smoking Status and Cessation Advice/Treatment | 5 | 4 | 7 | 4 | 5 | 5 | 6 | 10 | 46 | 5.75 | 7 |
| HgBA1c Poor Control | 9 | 9 | 10 | 7 | 10 | 10 | 7 | 10 | 72 | 9 | 11 |
| HgBA1c At Goal | 9 | 7 | 10 | 4 | 6 | 5 | 3 | 10 | 54 | 6.75 | 8 |
| Blood Pressure Poor Control | 9 | 10 | 10 | 8 | 10 | 10 | 9 | 10 | 76 | 9.5 | 11 |
| Blood Pressure Superior Control | 9 | 10 | 10 | 5 | 8 | 8 | 5 | 10 | 65 | 8.125 | 10 |
| LDL Poor Control | 8 | 8 | 10 | 8 | 8 | 9 | 8 | 10 | 69 | 8.625 | 10 |
| LDL Superior Control | 8 | 8 | 10 | 4 | 7 | 8 | 5 | 8 | 58 | 7.25 | 9 |
| Overall Diabetes Care Satisfaction | 1 | 3 | 5 | 5 | 2 | 7 | 8 | 6 | 37 | 4.625 | 6 |
| Self-care Support | 5 | 4 | 5 | 8 | 2 | 7 | 9 | 10 | 50 | 6.25 | 7 |
| Maximum | 9 | 10 | 10 | 8 | 10 | 10 | 9 | 10 | 76 | | 100 |

FIG. 8

| Measure | Criteria | Point Value | Product |
|---|---|---|---|
| Ophthalmologic Examination | 0.288 | 8 | 2.285 |
| Nephropathy Assessment | 0.731 | 9 | 6.675 |
| Podiatry Examination | 0.356 | 4 | 1.439 |
| Smoking Status and Cessation Advice/Treatment | 0.675 | 7 | 4.648 |
| HgBA1c Poor Control | 0.725 | 11 | 7.814 |
| HgBA1c At Goal | 0.36 | 8 | 2.91 |
| Blood Pressure Poor Control | 0.537 | 11 | 6.11 |
| Blood Pressure Superior Control | 0.169 | 10 | 1.644 |
| LDL Poor Control | 0.587 | 10 | 6.063 |
| LDL Superior Control | 0.238 | 9 | 2.066 |
| Overall Diabetes Care Satisfaction | 0.463 | 6 | 2.565 |
| Patient Self-care Support | 0.531 | 7 | 3.975 |
| | | Standard or Benchmark | 48.19 |

The poor control measures are reversed scored and therefore their criteria (in bold) are inverted (e.g., the criteria for LDL Poor Control was 41.3% and therefore 1 − 41.3% = 58.7%).

FIG. 9

```
libname ct "file location for patient level chart data";
libname pts "file location for patient level survey data";

libname bootsas "file location for bootstrapping data sets";
libname outsas "file location for physician level performance data";

*define cut score;
%let cutscore=48.19;

****part 1. Introduce criterion to each measure;
data results;
set outsas.bte_profile_new;
run;

data results;
set results;
*****chart data;
alc_gt9_cr=(alc_gt9_13) le .275;
alc_lt7_cr=(alc_lt7_13) ge .360 ;
bpge_90_140_cr=(bp_ge90_140) le .463;
bp_80_130_cr=(bp_80_130_rpt) ge .169;
ldlge130_cr=(ldl_ge130) le .413;
ldl100_cr=(ldl100_13) ge .238;

new_eyeexam_cr=eye_exam_new13 ge .288;
new_nephropathy_cr=urine_test_e_done13 ge .731;
footexam_cr=foot_exam_done13 ge .356;
smoking_cr=smoking_non_supp13 ge .675;

alc_rev=1-alc_gt9_13;
bp_rev=1-bp_ge90_140;
ldl_rev=1-ldl_ge130;

******part 2. Calculate a score for each physician, each measure;
array ct_item{10} alc_gt9_cr alc_lt7_cr bpge_90_140_cr bp_80_130_cr
     ldlge130_cr ldl100_cr new_eyeexam_cr
     new_nephropathy_cr footexam_cr smoking_cr;

array ct_item_r{10} alc_rev alc_lt7_13 bp_rev bp_80_130_rpt
     ldl_rev ldl100_13 eye_exam_new13
     urine_test_e_done13 foot_exam_done13 smoking_non_supp13;

array ct_item_0{10} alc_rev_0 alc_lt7_13_0 bp_rev_0 bp_130_80_0
     ldl_rev_0 ldl_lt100_0 eye_exam_new13_0
     neph_0 footexam smoking_nortrtm_0;

array ct_weight{10} _TEMPORARY_ (11 8 11 10 10 9 8 9 4 7);

do i=1 to 10;
ct_item_0(i)= min(of ct_item(i), ct_item_r(i));
end;
```

FIG. 11A

```
do i=1 to 10;
ct_score_h2=sum(of ct_score_h2, ct_item_h(i)*ct_weight(i));
end;

satis_cr=SC_OVERALL_CARE_P ge .463;
self_care_cr2=self_care_op ge .531;

array pt_weight{2} _TEMPORARY_ (7 9);

array pt_item2{2} satis_cr self_care_cr2;
array pt_item_r{2} SC_OVERALL_CARE_P self_care_op;
array pt_item_0{2} SC_OVERALL_CARE_P_0 self_care_op_0;

do i=1 to 2;
pt_item_0(i)= min(of pt_item2(i), pt_item_r(i));
end;

do i=1 to 2;
pt_score_r=sum(of pt_score_r, pt_item_r(i)*pt_weight(i));
end;

total_score_h2=ct_score_h2+pt_score_r;

if total_score_h2 ge &cutscore then elig_h2=1; else elig_h2=0;
run;

proc freq data=results;
tables elig_h2;
run;

proc means data=results mean std;
var total_score_h2;
run;
```

FIG. 11B

```
libname ct "file location for patient level chart data";
libname pts "file location for patient level survey data";

libname bootsas "file location for bootstrapping data sets";
libname outsas "file location for physician level performance data";

*Part 1. Define the variables we want to include in the bootstrap samples;
%let varct=%str(
alc_gt9_13
alc_lt7_13
bp_ge90_140
bp_80_130_rpt
ldl_ge130
ldl100_13
lipid_profile13
eye_exam_new13
foot_exam_done13
urine_test_e_done13
smoking_non_supp13
);

%let varpt=%str(
SC_OVERALL_CARE_P
SC_PRACT_CONCERN_P
SC_PRACT_ASK_QUES_P
SC_PRACT_EATING_PLAN_P
SC_PRACT_TAKEMEDS_P
SC_PRACT_SIDE_EFFECTS_P
SC_PRACT_FOOTCARE_P
SC_PRACT_BS_HOME_P
);

***Part 2. Generate patient-level bootstrap samples for chart data;
data indata;
set ct.dm2005_chrv_1260_bte_final;
keep candidate patient_id &varct;
run;

%include "SAS macro for generating bootstrapping sample.sas";
data bootsas.dm_ct_sizeg;
set outboot_size;
run;

******Part 3. Generate physician means for the bootstrap sample for chart data;
proc means data=bootsas.dm_ct_sizeg noprint;
var &varct;
output out=boot(drop=_type_) mean=&varct;
by candidate replicate;
run;

data bootsas.dm_ctphy_size;
set boot;
```

FIG. 12A

```
run;

******Part 4. Generate patient level bootstrap samples for patient survey
data;
data indata;
set pts.dm2005_ptsv_1260_bte_final;
keep candidate patient_id &varpt;
run;

%include "SAS macro for generating bootstrapping sample.sas";
data bootsas.dm_pt_sizeg;
set outboot_size;
run;

******d. Physician means for the bootstrap sample for patient survey data;
proc means data=bootsas.dm_pt_sizeg noprint;
var &varpt;
output out=boot(drop=_type_) mean=&varpt;
by candidate replicate;
run;

data bootsas.dm_ptphy_size;
set boot;
run;
```

```
******SAS macro for generating bootstrapping sample.sas****/
sasfile indata load;

Proc surveyselect data=indata out=outboot_size seed=12345
        Method=urs samprate=1 outhits Rep=1000;
Strata candidate;

Run;

sasfile indata close;
```

FIG. 12B

```
libname ct "file location for patient level chart data";
libname pts "file location for patient level survey data";

libname bootsas "file location for bootstrapping data sets";
libname outsas "file location for physician level performance data";

****Define macro variables and datasets;
%let ssize=25;
%let cutscore=48.19;

*****part 1. Reliability estimation for individual intermediate outcomes
measures;
*****part 1a. chart data;
%let bset1=bootsas.dm_ctphy_size;
%let dset1=ct.dm2005_chrv_1260_bte_final;

%let varct=%str(
a1c_gt9_13
a1c_lt7_13
bp_ge90_140
bp_80_130_rpt
ldl_ge130
ldl100_13
)
;
%let dataexe=dataexe;
data dataexe;
set &bset1 ;
run;

data list;
set &dset1;
run;

proc means data=list mean nway noprint;
class candidate;
var &varct;
    output out=physcores
    mean=&varct;
run;

data ct_profile;
set physcores;
run;

data physcores;
set physcores;
rename _freq_=pt_cnt;
run;
*****Retain number of patients per physician in each data set;
data ctpt_cnt;
set physcores;
keep candidate pt_cnt;
run;
```

FIG. 13A

```
data ptcnt;
set ctpt_cnt;
run;

%include "reliability macro.sas";
proc export data=reli
outfile="c:\temp\excel export\reli_ct_ind.csv"
dbms=csv replace;
run;

*****Part 1b. patient survey data;
%let dset1=pts.dm2005_ptsv_1260_bte_final;
%let bset1=bootsas.dm_ptphy_size;

%let varct=%str(
SC_OVERALL_CARE_P
SC_PRACT_CONCERN_P
SC_PRACT_ASK_QUES_P
SC_PRACT_EATING_PLAN_P
SC_PRACT_TAKEMEDS_P
SC_PRACT_SIDE_EFFECTS_P
SC_PRACT_FOOTCARE_P
SC_PRACT_BS_HOME_P
)
;

data dataexe;
set &bset1 ;
run;

proc means data=&dset1 mean nway noprint;
class candidate;
var &varct;
    output out=physcores
    mean=&varct;
run;

data physcores;
set physcores;
rename _freq_=pt_cnt;
run;

*****Retain number of patients per physician in each data set;
data ptpt_cnt;
set physcores;
keep candidate pt_cnt;
run;

data ptcnt;
set ptpt_cnt;
run;

%include "reliability macro.sas";
proc export data=reli
```

FIG. 13B

```
outfile="C:\temp\excel export\reli_pt_ind.csv"
dbms=csv replace;
run;

******end of part 1;

************Part 2. Estimate reliability for overall score and four
individual chart process measures;
*****Define macro to generate score;
%macro score_gen;
data profile_ct;
set profile_ct;
*****chart data;
alc_gt9_cr=(alc_gt9_13) le .275;
alc_lt7_cr=(alc_lt7_13) ge .360 ;
bpge_90_140_cr=(bp_ge90_140) le .463;
bp_80_130_cr=(bp_80_130_rpt) ge .169;
ldlge130_cr=(ldl_ge130) le .413;
ldl100_cr=(ldl100_13) ge .238;

new_eyeexam_cr=eye_exam_new13 ge .288;
new_nephropathy_cr=urine_test_e_done13 ge .731;
footexam_cr=foot_exam_done13 ge .356;
smoking_cr=smoking_non_supp13 ge .675;

if alc_gt9_cr=1 and bpge_90_140_cr=1 and ldlge130_cr=1 then b_three=1;
else b_three=0;

alc_rev=1-alc_gt9_13;
bp_rev=1-bp_ge90_140;
ldl_rev=1-ldl_ge130;

array ct_item{10} alc_gt9_cr alc_lt7_cr bpge_90_140_cr bp_80_130_cr
    ldlge130_cr ldl100_cr new_eyeexam_cr
    new_nephropathy_cr footexam_cr smoking_cr;

array ct_item_r{10} alc_rev alc_lt7_13 bp_rev bp_80_130_rpt
    ldl_rev ldl100_13 eye_exam_new13
    urine_test_e_done13 foot_exam_done13 smoking_non_supp13;

array ct_item_0{10} alc_rev_0 alc_lt7_13_0 bp_rev_0 bp_130_80_0
    ldl_rev_0 ldl_lt100_0 eye_exam_new13_0
    neph_0 footexam smoking_nortrtm_0;

array ct_weight{10} _TEMPORARY_ (11 8 11 10 10 9 8 9 4 7);

do i=1 to 10;
ct_item_0(i)= min(of ct_item(i), ct_item_r(i));
end;

do i=1 to 10;
ct_score=sum(of ct_score, ct_item(i)*ct_weight(i));
ct_score_r=sum(of ct_score_r, ct_item_r(i)*ct_weight(i));
ct_score_0=sum(of ct_score_0, ct_item_0(i)*ct_weight(i));
ct_score_h2=sum(of ct_score_h2, ct_item_h(i)*ct_weight(i));
ct_score_h=sum(of ct_score_h, ct_item_x(i)*ct_weight(i));
```

FIG. 13C

```
end;

data profile_pt;
set profile_pt;
satis_cr=SC_OVERALL_CARE_P ge .463;
self_care_cr2=self_care_op ge .531 ;

array pt_weight{2} _TEMPORARY_ (7 9);

array pt_item2{2} satis_cr self_care_cr2;
array pt_item_r{2} SC_OVERALL_CARE_P self_care_op;
array pt_item_0{2} SC_OVERALL_CARE_P_0 self_care_op_0;

do i=1 to 2;
pt_item_0(i)= min(of pt_item2(i), pt_item_r(i));
end;

do i=1 to 2;
pt_score=sum(of pt_score, pt_item2(i)*pt_weight(i));
pt_score_R=sum(of pt_score_r, pt_item_r(i)*pt_weight(i));
pt_score_0=sum(of pt_score_0, pt_item_0(i)*pt_weight(i));
end;

%mend;

*******define variables list;
%let varct=%str(
      eye_exam_newl3_0
      neph_0
      footexam
      smoking_nortrtm_0
      ct_score_h2
);
%let varpt=%str(
self_care_op
pt_score_r
)
;

******original data set;
data profile_pt;
set outsas.bte_profile_new;
run;
data profile_ct;
set outsas.bte_profile_new;
run;

%score_gen;
run;

data physcores;
merge profile_ct profile_pt;
by candidate;
total_score_h2=ct_score_h2+pt_score_r;
keep candidate &varct &varpt total_score_h2 ;
run;
```

FIG. 13D

```
*****export score descriptive statistics;
proc export data=physcores
outfile="c:\temp\excel export\dm_temp.csv"
dbms=csv replace;
run;

proc means data=physcores noprint;
output out=phy_mean(drop=_type_ _freq_ ct_score: pt_score:) mean=&varct
&varpt total_score_h2;
var &varct &varpt total_score_h2;
run;

proc export data=phy_mean
outfile="C:\temp\excel export\phy_mean.csv"
dbms=csv replace;
run;

proc means data=physcores noprint;
output out=phy_std(drop=_type_ _freq_ ct_score: pt_score:) mean=&varct &varpt
total_score_h2;
var &varct &varpt total_score_h2;
run;

proc export data=phy_cnt
outfile="C:\temp\excel export\phy_std.csv"
dbms=csv replace;
run;

*****Bootstrap dataset;
*original sample size;
data profile_ct;
set bootsas.dm_ctphy_size;
rename alc_gt9_15=alc_gt9_13
alc_goal_15_new=alc_lt7_13
bp_ge90_140=bp_ge90_140
bp_80_130_rpt=bp_80_130_rpt
ldl_ge130_15=ldl_ge130
ldl100_15=ldl100_13
eye_exam_new15=eye_exam_new13
foot_exam_done15=foot_exam_done13
urine_test_e_done15=urine_test_e_done13
smoking_non_supp15=smoking_non_supp13
;
run;
run;
data profile_pt;
set bootsas.dm_ptphy_size;
run;
%score_gen;
run;

data size_score;
merge profile_ct profile_pt;
by candidate replicate;
total_score_h2=ct_score_h2+pt_score_r;
keep candidate &varct &varpt total_score_h2 ;
```

FIG. 13E

```
run;

%let dataexe=size_score;
%include "reliability macro.sas";
proc export data=reli
outfile="C:\temp\excel export\reli_ct_score.csv"
dbms=csv replace;
run;

******Save the data for the next step;
data reli_c;
set reli;
run;

data n_zero_c;
set n_zero;
keep n_zero;
run;

******Generate results for patient survey;

%let varct=&varpt;
data ptcnt;
set ptpt_cnt;
run;
%include "reliability macro.sas";
proc export data=reli
outfile="C:\temp\excel export\reli_pt_score.csv"
dbms=csv replace;
run;

******Save the data for the next step;
data reli_p;
set reli;
run;
data n_zero_p;
set n_zero;
keep n_zero;
run;

******end of part 2;

*******Part 3. The overall reliability if we combine chart and patient score
together;
*******define variables list;
proc corr data=physcores out=corr noprint;
var total_score_h2 ct_score_h2 pt_score_r;
run;
proc export data=corr
outfile="C:\temp\excel export\reli_corr.csv"
dbms=csv replace;
run;

******Part 4. Decision consistency;
%include "SAS macro for decision consistency.sas";
```

FIG. 13F

```
proc export data=consist_a
outfile="c:\temp\excel export\consist_a.csv"
dbms=csv replace;
run;

data cand_con;
merge physcores (keep=candidate over_score:) cand_con;
by candidate;
run;

proc export data=cand_con
outfile="c:\temp\excel export\cand_con.csv"
dbms=csv replace;
run;

******end of part 4;
```

```
/***************reliability macro.sas***************/
*****Calculate the observed standard deviation;
******cluster size;
proc means data=ptcnt noprint;
output out=n_zero (drop=_type_) mean=nmean std=nstd;
var pt_cnt;
run;

data n_zero;
set n_zero;
n_zero=nmean-nstd*nstd/(_freq_*nmean);
call symput('n_zero', n_zero);
run;

proc means data=physcores noprint;
var &varct;
OUTPUT OUT=phmean(drop=_type_ _freq_) mean=&varct;
run;
proc means data=physcores noprint;
var &varct;
OUTPUT OUT=phstd(drop=_type_ _freq_) std=&varct;
run;

proc transpose data=phmean out=phmean prefix=phmean;
proc sort; by _name_;
run;

proc transpose data=phstd out=phstd prefix=phstd;
proc sort; by _name_;
run;

******Calculate the measurement error;

proc means data=&dataexe noprint;
var &varct;
output out=bootsd std=&varct;
by candidate;
```

FIG. 13G

```
run;

data bootsd_2;
merge bootsd ptcnt;
by candidate;
array v1 &varct;
do over v1;
v1=v1*v1*pt_cnt;
end;
run;

proc means data=bootsd_2 noprint;
var &varct pt_cnt;
output out=ssquare(drop=_type_ _freq_) sum=&varct pt_cnt;
run;

data ssquare;
set ssquare;
array v1 &varct;
do over v1;
v1=v1/pt_cnt;
end;
run;

proc transpose data=ssquare out=sem prefix=var;
run;

data sem;
set sem;
sem=sqrt(var1);
cnt=_n_;
run;

proc sort; by _name_;
run;

data reli;
merge phstd sem;
by _name_;
reli=(phstd1**2-var1)/phstd1**2;
reli_icc=reli/(&n_zero-reli*(&n_zero-1));
reli_icc25=25*reli_icc/(1+(25-1)*reli_icc);
rename var1=var_size;
run;

proc sort data=reli;
by cnt;
run;

%put &n_zero;
run;
```

```
/*********SAS macro for decision consistency.sas*************/
*****1. Pull out scores for the next step;
```

FIG. 13H

```
data observ;
set physcores;
keep candidate total_score_h2;
rename
      total_score_h2=obs_over2
;
run;

data size;
set size_score;
keep candidate replicate total_score_h2;
rename
      total_score_h2=size_over2
;
run;

data all;
merge observ size;
by candidate;
run;

%macro con_de;

******2. Both parts, consistency;
%let conlist=%str(
con_size_over2
)
;
%let bilist=%str(
bi_con_size_over2
);

data varlist;
set varlist2;
id=_n_;
cnt=1;
run;

data varlist;
set varlist;
by cnt;
if last.cnt then output;
call symput('varcnt', id);
run;

data ct_score;
set all;
con_size_over2=0;

if (obs_over2 ge &score and size_over2 ge &score) or (obs_over2 lt &score and
size_over2 lt &score)
   then con_size_over2=1;
run;

proc means data=ct_score noprint;
output out=temp1(drop=_type_ _freq_)
```

FIG. 13I

```
      mean=&conlist;
var &conlist;
by candidate;
run;

data templ;
set templ;
array org{&varcnt} &conlist;
array bi{&varcnt} &bilist;
do i=1 to &varcnt;
bi{i}=org{i}*org{i}+(1-org{i})*(1-org{i});
end;
drop i;
run;

data cand_con;
set templ;
run;

proc means data=templ noprint;
output out=tcon1(drop=_type_ _freq_)
    mean=&conlist &bilist;
var &conlist &bilist;
run;

data consist_a;
   retain score;
   set tcon1 (keep=&conlist &bilist);
   score=&score;
   run;

%mend con_de;

data varlist2;
input varlist $15.;
cards;
con_size_over2
;
run;
%con_de;
run;
```

FIG. 13J

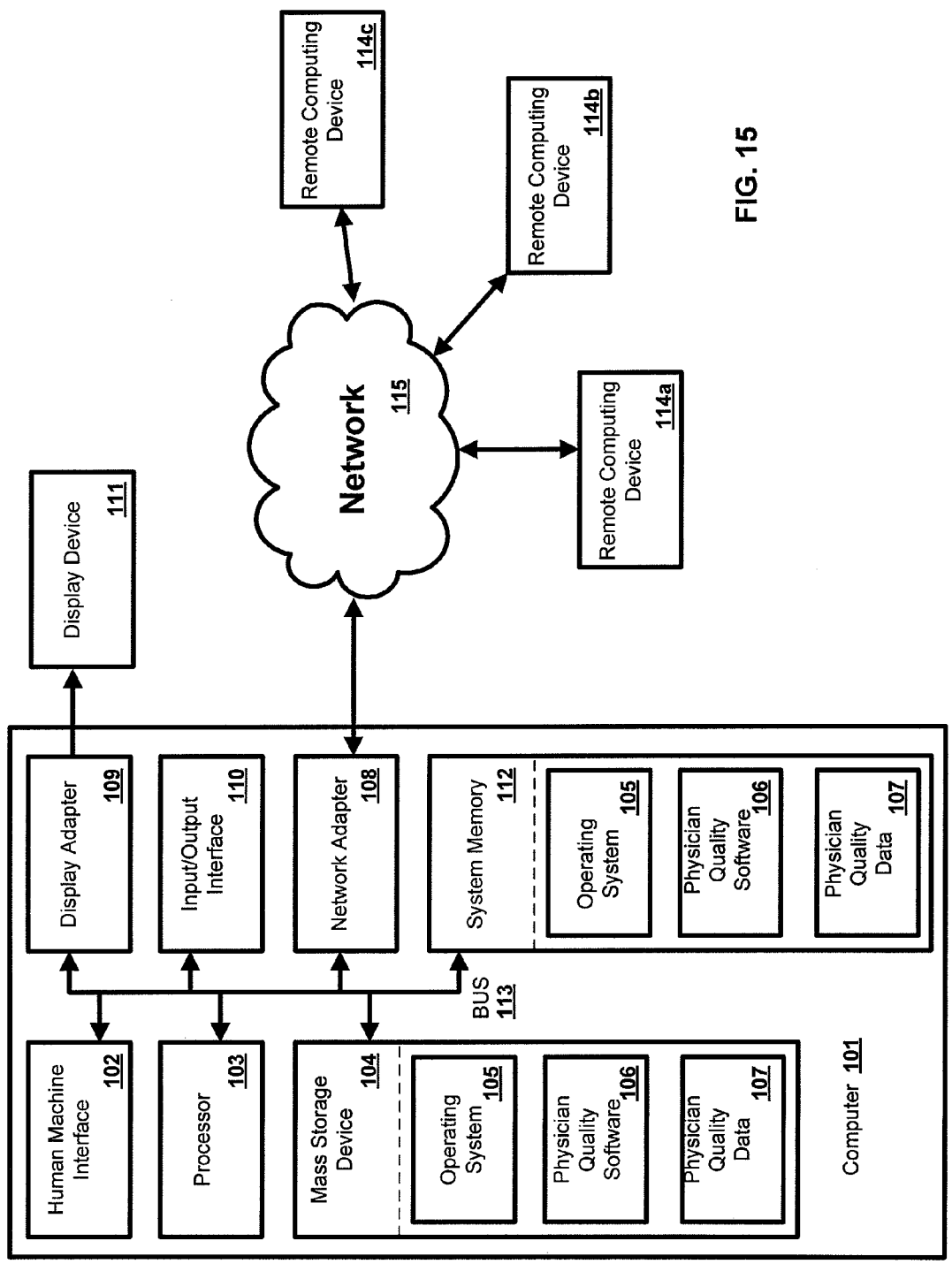

METHOD AND SYSTEM FOR DETERMINING A FAIR BENCHMARK FOR PHYSICIANS' QUALITY OF PATIENT CARE

BACKGROUND

The performance of physicians in their daily clinical practices has become an area of intense public interest. Both patients and healthcare purchasers want more effective means of identifying good clinical care, and therefore a variety of organizations, such as the National Commission on Quality Assurance (NCQA) and Bridges to Excellence®, have developed recognition and pay-for-performance programs that reward physicians, hospitals, medical groups, and other healthcare providers for meeting certain performance criteria for quality and efficiency. These types of programs reward participating physicians who are categorized as "top performers" in diabetes care either with a particular fee to the physician for each diabetic patient covered by a participating health plan and/or employer or a recognition award. Physicians submit data for a sample of patients on specific performance measures, such as intermediate outcome measures (e.g., blood pressure levels), process measures (e.g., smoking cessation counseling), and patient experience measures (e.g., patient satisfaction). A physician's performance is calculated by awarding points for each measure achieved, summing the points to yield an overall score, which is then compared to specific levels of recognition and/or payment. While this scoring procedure is easy to calculate, the process to derive the performance criteria, specific point values, and overall performance benchmark by which physicians are being assessed is not based on a rigorous methodology and may be unintentionally misclassifying physician performance.

To assess the performance of physicians a set of evidence-based performance measures are used that pertain to the care of patients with a particular disease condition. For example, three intermediate outcome measures (hemoglobin $A_{1c}$ levels, lipid levels, and blood pressure at last visit) and four process measures (ophthalmologic examination, podiatry examination, nephropathy assessment, and smoking status or cessation advice/treatment) are used in many programs because they are supported by evidence-based guidelines established by the American Diabetes Association that describe ideal care for diabetic patients (American Diabetes Association, 2008). For each intermediate outcome measure, there is a minimally acceptable, evidence-based level of performance. For example, patients with low-density lipoprotein cholesterol (LDL) levels <100 mg/dl have superior control of their LDL. The performance rate for each measure is typically defined as the percent of a physician's patient panel that met the minimally acceptable level. For all process measures, performance rate is defined as the percent of a physician's patient panel that received the test/exam or counseling. Some programs also provide an optional set of patient experience measures (collected from a patient survey) that may be included as measures in the assessment.

A physician's performance is typically assessed by awarding a specific number of points (or scoring weight) for each measure if the measure's minimum performance criterion is met, but there is no specific methodology or system used to determine how the points are derived. For example, physicians may receive 5 points if at least 80% of their panel of diabetes patients received a podiatry examination. If less than 80% of their patients received a podiatry examination, then they are awarded 0 points. Some programs institute multiple benchmarks, or "tiers" of performance recognition (e.g., above average, very good, and exceptional performance) based on total number of points earned and these are used to determine the amount of compensation paid to the participating physician.

These old methods for assessing physician's performance in practice do not use a rigorous process based on established measurement principles to determine (1) the minimum performance criteria for individual measures, (2) importance of individual measures relative to one another (i.e., weighting or point value), and (3) an overall minimum performance standard or benchmark for managing a specific disease. Limitations with the method used to compute overall performance scores also exist; that is, awarding physicians all of the points allocated to a measure if they satisfy the measure's minimum criterion, and no points if they do not. First, the old method rewards the same number of points to physicians who just barely met the minimum performance criterion for an individual measure as to those who exceeded the minimum performance criterion by a significant amount. Second, when the minimum performance criteria are set very low the distribution of total points that physicians earn is quite skewed and distinguishing one physician from another is more difficult. Third, currently there are no measurement techniques consistently being used to assess whether the measurements that are obtained are meaningful in terms of their reliability and decision consistency of the performance benchmark. High reliability is essential in determining whether the method of measurement is fair, consistent, and accurate to be credible to the public. Reliability measures the proportion of true ability measured by the method rather than measurement error and can be computed for an individual measure or composite measures. High decision consistency is also critical since it judges how consistent are the decisions that are made about physician performance at a particular performance standard over many different samples of patients; the consistency of the standard (i.e., benchmark) should be high so that there are fewer false classifications (e.g., physicians who are incorrectly classified as providing good patient care).

Therefore, what are needed are systems and methods that overcome challenges found in the present state of the art, some of which are described above.

SUMMARY

Described herein are embodiments of methods, systems and computer program products for determining performance criteria, specific point values, and performance benchmarks that can be used to assess physicians in practice. To achieve a credible assessment of physicians that could distinguish one physician from another, as well as recognize or reward through payment those who are providing good clinical care, a sound methodology acceptable by measurement experts and the public is proposed.

In one aspect, a methodology for defining a benchmark for physician performance in the delivery of patient care in a particular clinical domain is provided. This method comprises calculating an overall performance score for a physician by determining performance criteria and point values (or scoring weights) for individual measures and then setting a performance standard or benchmark for patient care in the specific clinical domain. To facilitate a description of the embodiments of the invention, an example is provided of diabetes care performance using hypothetical data. In order to assess physicians' performance in clinical practice, physicians identify a panel of patients for whom measure data are available. For example, physicians certified in internal medicine or one of its subspecialties can obtain practice performance data by completing the ABIM Diabetes PIM Practice Improvement Module® developed by the American Board of Internal Medicine (ABIM) which targets care of diabetic patients. The ABIM Diabetes PIM is a web-based, self-evaluation tool that guides physicians through collecting data from their own practice, using medical chart reviews, patient surveys, and a practice-system survey to create a comprehensive practice performance assessment.

Described herein are methodologies, systems and computer program products to address deficiencies in the practice assessment arena in determining performance benchmarks for individual physicians in clinical practice using a "continuous" point scoring method, which uses more information from a physician's performance on each measure than a dichotomous scoring method, making it more sensitive to identifying differences among physicians. The reliability of individual measures and overall performance scores can be evaluated, as well as the decision consistency of the performance standard determined by an expert panel to ensure a robust and fair physician assessment.

Additional advantages will be set forth in part in the description which follows or may be learned by practice. The advantages will be realized and attained by means of the elements and combinations particularly pointed out in the appended claims. It is to be understood that both the foregoing general description and the following detailed description are exemplary and explanatory only and are not restrictive, as claimed.

BRIEF DESCRIPTION OF THE DRAWINGS

The accompanying drawings, which are incorporated in and constitute a part of this specification, illustrate embodiments and together with the description, serve to explain the principles of the methods and systems:

FIG. 1 illustrates the intermediate outcome, process, and patient experience measures from the ABIM Diabetes PIM used to assess physicians' performance in diabetes care;

FIG. 2A is an exemplary flowchart illustrating an overview process for assessing a particular physician's practice performance according to an embodiment of the invention;

FIG. 3 presents an example of patient characteristics from a general internal medicine physician population;

FIG. 4 illustrates an exemplary rating sheet;

FIG. 6 presents an exemplary spreadsheet that can be used to calculate the average final Angoff ratings across raters for each measure;

FIG. 7 illustrates an exemplary ratings sheet for each member of the expert panel to record his or her Importance ratings;

FIG. 8 illustrates an exemplary spreadsheet for averaging the Importance rankings;

FIG. 9 presents an exemplary spreadsheet that can be used to calculate the performance standard or benchmark;

FIGS. 11A and 11B shown an actual exemplary SAS® program for implementing the process of FIG. 10B;

FIGS. 12A and 12B present an exemplary SAS® program for generating bootstrap samples;

FIGS. 13A-13J present an exemplary SAS® program for estimating reliability of the individual measures and overall performance scores, as well as for estimating the decision consistency of the standard;

FIG. 15 is a block diagram illustrating an exemplary operating environment for performing the disclosed methods.

DETAILED DESCRIPTION

Figure 2B:
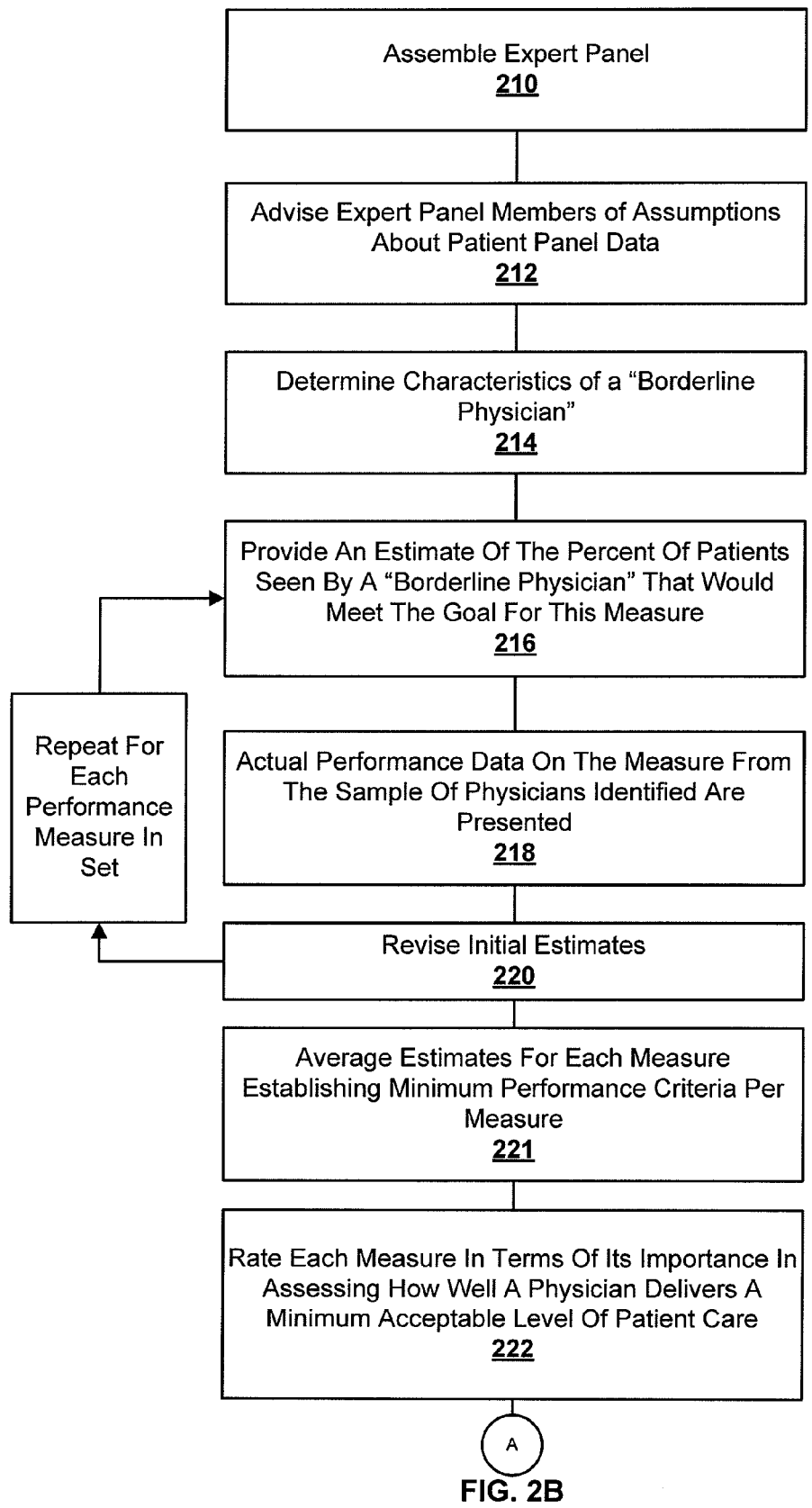
FIGS. 2B and 2C present an exemplary flowchart of the steps used to determine a fair benchmark for assessing physicians' quality of patient care.

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the Examples included therein and to the Figures and their previous and following description.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

Overview:

It is well accepted in the literature that a set of performance measures should be clinically important, relevant to practice, psychometrically/statistically sound, and feasible to collect (Landon et al., 2003). For example, the intermediate outcome, process, and patient experience measures from the ABIM Diabetes PIM used to assess physicians' performance in diabetes care are shown in FIG. 1. For each intermediate outcome measure there is a minimally acceptable, evidence-based level of performance (e.g., patients with blood pressure levels <130/80 have superior control of their blood pressure, while patients with level ≧140/90 have poor control of their blood pressure) developed by the NCQA in partnership with the American Diabetes Association. A physician's performance rate for each intermediate outcome measure is defined as the percent of his or her patient panel that met the minimally acceptable level. For process measures, performance is defined as the percent of his or her patient panel that received the test/exam or counseling. For the patient experience measures, overall diabetes care satisfaction is defined as the percent of patients who rated their overall diabetes care "excellent" or "very good" based on one patient survey question using a five-point Likert-type rating scale. Patient self-care support is defined as the percent of patients who provided "excellent" or very good" responses to seven patient survey questions regarding patient self-care support (i.e., showing an understanding of living with diabetes, encouraging questions and answering them clearly, providing information on taking medications properly, providing information on medication side effects, teaching foot care, providing information on proper diabetic diet, and teaching home blood glucose monitoring). The patient experience measures of overall diabetes care satisfaction and patient self-care support were drawn from the NRC Picker Patient Survey and further modified based on results of a pilot study conducted by the ABIM. The use of "very good" and "excellent" to define quality patient experience is consistent with patient satisfaction measures used by the Health Quality Council.

FIG. 2A is an exemplary flowchart illustrating an overview process 200 for assessing a particular physician's practice according to an embodiment of the invention. At step 202, patient-level data specific to the performance of a plurality of physicians is received. At step 204, physician-level data related to the plurality of physicians' performance is received. At step 206, minimum performance criteria for individual measures are developed, as further described herein. At step 208, the minimum performance criteria for the individual measures set are applied to data specific to a physician, and the physician is assigned an overall performance score, which can be used to determine whether the particular physician achieved the benchmark. In one aspect, the process of FIG. 2A can be implemented in a client-server environment, as known to one of ordinary skill in the art, whereby physicians, patients, prospective patients, etc. can obtain score information about a physician or group of physicians.

Figure 2C:
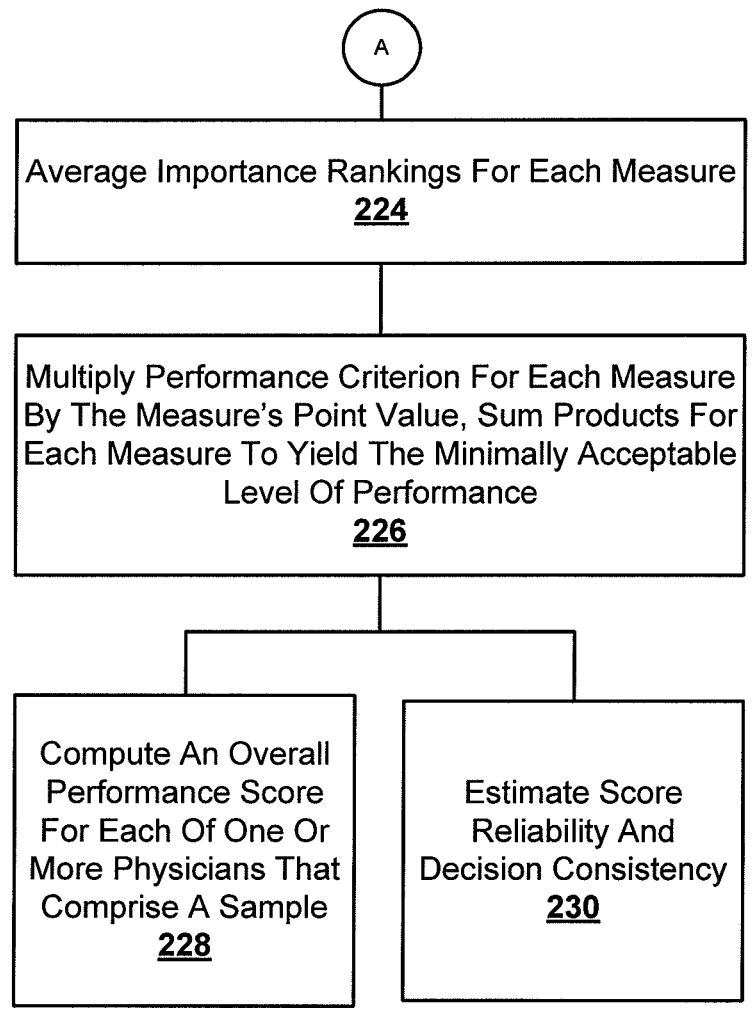

FIGS. 2B and 2C present an exemplary flowchart of the steps used to determine a fair benchmark for assessing physicians' quality of patient care. The minimum performance criteria for the individual measures set is established through a structured, rigorous process. In one aspect, the minimum performance criteria are determined through the Angoff standard-setting methodology (Angoff W H. Scales, norms, and equivalent scores. In R. L. Thorndike (Ed.), *Educational Measurement* (2nd ed., pp. 508-600). Washington, D.C.: American Council on Education; 1971; and Ricker K L. Setting cut scores: Critical review of the Angoff and modified Angoff methods. *Alberta J Educ Res.* 2006; 52:53-64; both of which are incorporated herein by reference and as known to one of ordinary skill in the art) as applied to physician practice performance measures. The Angoff method is widely used for setting performance standards, or minimum passing scores, on multiple-choice examinations. Other examples of methods used for multiple choice exams include the Bookmark, Nedelsky and Hofstee methods (In G. J. Cizek (Ed), *Setting Performance Standards: Concepts, Methods, and Perspectives.* Mahwah, N J: Lawrence Erlbaum Associates; 2001; incorporated herein by reference and as known to one of ordinary skill in the art). In standardized or simulation-based performance assessments, the minimum performance criteria are determined using, for example, work-centered approaches (McKinley D W, Boulet J R, & Hambleton R K. A work-centered approach for setting passing scores on performance-based assessments. *Eval Health Prof.* 2005; 28:349-369; and Boulet J R, De Champlain A F, & McKinley D W. Setting defensible performance standards on OSCEs and standardized patient examinations. *Med Teach.* 2003; 25: 245-249; both of which are incorporated herein by reference and as known to one of ordinary skill in the art).

Referring to the exemplary flowchart of FIGS. 2B and 2C, to implement the illustrated process, data from a representative sample of physician practices of clinical and patient satisfaction measures is received and used. At step 210, the process begins by selecting and convening an expert panel committee comprised of, for example, at least eight physicians with expertise in caring for patients with the target disease condition though greater or fewer numbers of experts are also contemplated. In one aspect, the panel convenes vie electronic means, such as teleconference, videoconference, or via computer-facilitated conferencing or meeting systems such as, for example, WebEx™ (available from Cisco Systems, Inc.), among others. In one aspect, at step 212 of the standard-setting procedure, the expert panel is advised of certain assumptions about the patient panel data. Preferably, the members of the expert panel will agree to embrace these assumptions. These assumptions depend on limitations of the dataset. Assumptions can include, for example, one or more of (1) that the patient characteristics are from an average general physician practice if no formal risk adjustment calculation is used to adjust for patient case-mix differences; (2) that the data may be somewhat inflated if the performance data are strictly self-reported, physicians are volunteers, and there is no practice audit; (3) that practice system differences should not be risk-adjusted out; and (4) the set of performance measures is adequate.

To determine performance criteria for the set of measures, at step 214 the expert panel determines one or more characteristics of a "borderline physician." In one aspect, this involves the members of the expert panel discussing the characteristics of a physician who demonstrates a minimum acceptable level of performance in caring for a specific patient population, such as diabetic patients (referred to as the "borderline physician"). During this discussion the proposed characteristics are recorded and provided to the panel as they are developed. This can comprise, for example, displaying these characteristics on a screen, computer display, etc. for the expert panel to examine, or verbally providing the information to the panel. To assist the expert panel to conceptualize the "borderline physician," a set of descriptive statistics describing patient characteristics obtained from the relevant physician population is offered. For example, FIG. 3 presents patient characteristics from a general internal medicine physician population.

Figure 5:
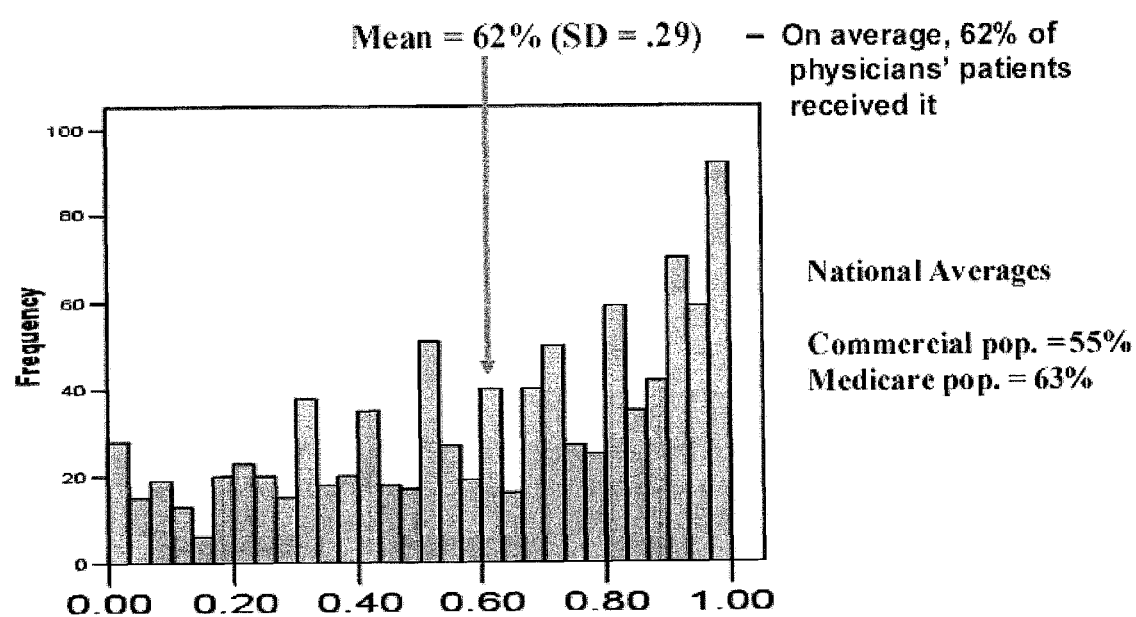
FIG. 5 illustrates exemplary summary performance data for an ophthalmologic examination measure and the two national data sources.

After the expert panel compiles a list of the characteristics of the "borderline physician," at step 216 the expert panel is presented with the first performance measure and each member of the expert panel is asked to provide an estimate of the percent of patients seen by a "borderline physician" that would meet the goal for this measure. For example, an expert panel may be asked the question "what percent of diabetic patients seen by a borderline physician would receive an ophthalmologic examination?" Each member is asked to record their initial estimate next to the measure in a rating sheet such as the exemplary one shown in FIG. 4. The facilitator collects the panel's initial ratings and presents them on the screen so that the expert panel may discuss their ratings with the intent of resolving extreme differences among raters. At step 218, the expert panel is then presented with the actual results on the measure from a representative sample of physicians, along with any other performance criteria (e.g., averages for Medicare patients). For example, summary performance data for an ophthalmologic examination measure and the two data sources are shown in FIG. 5. FIG. 5 shows that, on average, 62% of patients in a representative sample of 957 physician practices received an ophthalmologic examination. The Medicare population physician average is 63% while the commercial population physician average is 55%. At step 220, following review of these summary performance data, the expert panel is given an opportunity to discuss and revise their initial Angoff estimates. Final Angoff estimates are recorded on the record sheet, and then these final estimates are provided to the expert panel so they can review and approve them. The process for collecting initial and final Angoff estimates is repeated for each individual measure in the assessment. At step 221 after all of the final Angoff estimates are recorded, raters' final estimates are averaged for each measure. These average estimates become the minimum performance criterion for each respective measure. FIG. 6 presents an exemplary spreadsheet that can be used to calculate the average final Angoff estimates across raters for each measure. The collection of initial and final estimates and averaging can be performed automatically via a computer system as each panel member submits their ratings. For example, the average final estimates across eight raters for the ophthalmologic examination measure is 28.5%, representing the minimum performance criterion for this measure.

After the expert panel determines the minimum performance criteria for the set of measures, the raters assign the importance weights (or points) for each of the measures, which are used to compute an overall performance score for a physician. To complete this task, at step 222 the expert panel independently rates each measure in terms of its importance in assessing how well a physician delivers a minimum acceptable level of patient care. To do this they use, for example, an 11-point Likert scale with 0=Not At All Important and 10=Very Important. Each member of the expert panel records his or her Importance ratings using a record sheet, such as the exemplary sheet shown in FIG. 7. As known to one of ordinary skill in the art, the rating sheet can be provided electronically to the raters and the panel can submit their sheets electronically. In one aspect, a unique rating sheet is created for each individual rater with the set of measures listed in random order so that the effect of presentation order is controlled when experts rate the importance of each measure. At step 224, individual record sheets from each rater are received, and for each measure the importance ratings are averaged across all raters using, for example, a spreadsheet such as the one shown in FIG. 8. In one aspect, a Dunn-Rankin scaling method (Dunn-Rankin P. *Scaling Methods*. Hillsdale, N.Y.: Lawrence Erlbaum; 1983, incorporated herein by reference and as known to one of ordinary skill in the art) can be used to calculate weights for each measure, which incorporates both the average importance rating and the maximum rating provided by each rater so that the sum of the weights will range from 0 to 100. This calculation is shown in the "Points" column on the far right side of the spreadsheet shown in FIG. 8. For example, the ophthalmologic examination measure is assigned a weight of 8 points.

Computing the Standard or Benchmark

To determine an overall performance standard or benchmark, at step 226 the minimum performance criterion for each individual measure is multiplied by the assigned point value. Then the products for each measure are summed to yield the minimum number of total points that a physician must earn to satisfy the minimally acceptable level of overall performance. These calculations, as with all of the steps of this process, can be performed by a computer. FIG. 9 presents an exemplary spreadsheet that can be used to calculate the overall performance standard or benchmark.

Computing Overall Performance Scores

Once the performance criteria and point values for the measures set are determined, at step 228, a computer can be programmed to compute an overall performance score for each of one or more physicians that comprise a sample. At step 230, a computer can also be programmed to estimate score reliability and decision consistency.

Figure 10A:
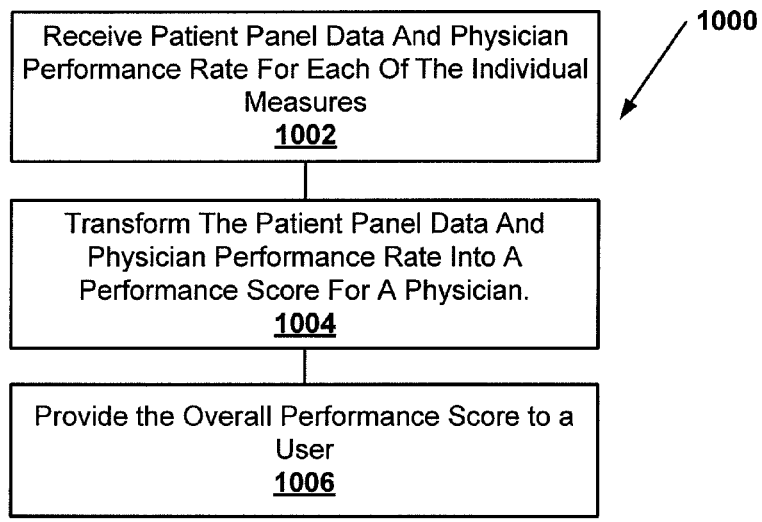
FIG. 10A illustrates an exemplary flowchart for calculating a performance score for a physician.

FIG. 10A illustrates an exemplary flowchart 1000 for calculating an overall performance score for a physician. At step 1002, patient panel data and physician performance rate for each of the individual measures is input or received into the computer. At step 1004, the received patient panel data and physician performance rate is used in cooperation with the performance criteria and point values assigned to the measures set to transform the patient panel data and physician performance rate into a performance score for a physician. To compute an overall performance score for a physician, the physician's actual performance rate for each individual measure is multiplied by its assigned point value. For example, if a physician performed a podiatry examination on 65% of patients in her panel and it is weighted 4 points, then she would receive 2.6 points for this measure (0.65×4=2.6). Points earned for individual measures are then summed to yield a total score between 0 and 100 points. Depending on the purpose of the assessment, the computer can be programmed to exercise some flexibility in scoring a physician. For example, in situations where physicians are believed to have direct control of clinical processes, the minimal performance criteria for the process measures can be used as a lower bound for scoring (i.e., if the percent of a physician's patients fell below the criterion for an individual process measure, then the physician would earn zero points for that measure). For example, if only 20% of patients received the ophthalmology exam, then one would receive no points, but if 28.5% of patients received the ophthalmology exam, then one would begin to earn points. As another example, risk adjustors can be incorporated to adjust physicians' actual performance rates. That is, it may be important to account for differences in patient characteristics, such as age and general health status. This is to account for the situation where physicians who treat primarily older, less healthy patients appear to be providing lower quality of care than physicians treating primarily younger, healthy patients. At step 1006, the computed overall performance score is provided to a user.

Figure 10B:
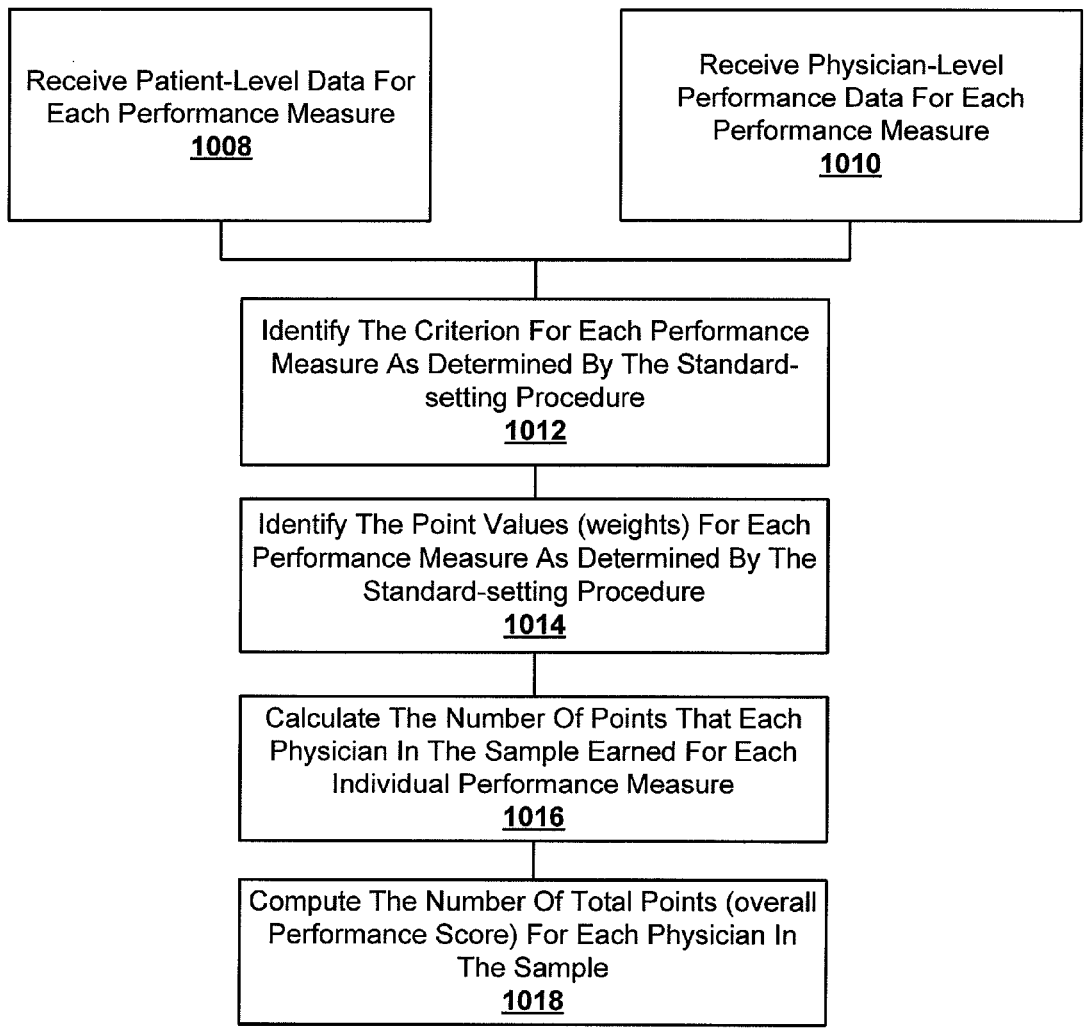
FIG. 10B illustrates an exemplary flowchart for a process that computes points for individual measures and for the total performance score.

In one aspect, the process described in FIG. 10A can be implemented in, for example, a SAS® program (SAS Institute, Inc, Cary, N.C.), though other programming languages and hardware implementations are contemplated within the scope of the embodiments of this invention. FIG. 10B illustrates an exemplary flowchart for a process that computes points for individual measures and for the overall performance score. An actual exemplary SAS® program for implementing the process of FIG. 10B is shown in FIGS. 11A and 11B. In order to use this exemplary SAS® program, input datasets are generated outside of the standard-setting and scoring processes. For the diabetes care assessment example, datasets comprise a list of physicians with their patient-level performance on the clinical measures and patient experience measures 1008, respectively, and another dataset 1010 includes performance data on all measures at the physician level. The SAS® program can be modified to fit other sets of measures used in practice assessments other than diabetes care. At step 1012, the criterion for each performance measure as determined by the standard-setting procedure as described in FIG. 2B is identified (or existing criterion are retrieved and used). At step 1014, the point values (weights) for each performance measure as determined by the standard-setting procedure as described in FIG. 2B are identified (or existing point values are retrieved and used). At step 1016, the number of points that each physician in the sample earned for each individual performance measure are calculated. At step 1018, the number of total points (overall performance score) for each physician in the sample is computed. Once overall performance scores for each physician in a sample are determined, these scores can be analyzed using standard statistics tools such as frequency distribution, mean, median, mode, and standard deviation.

Estimating Score Reliability and Decision Consistency

Figure 14:
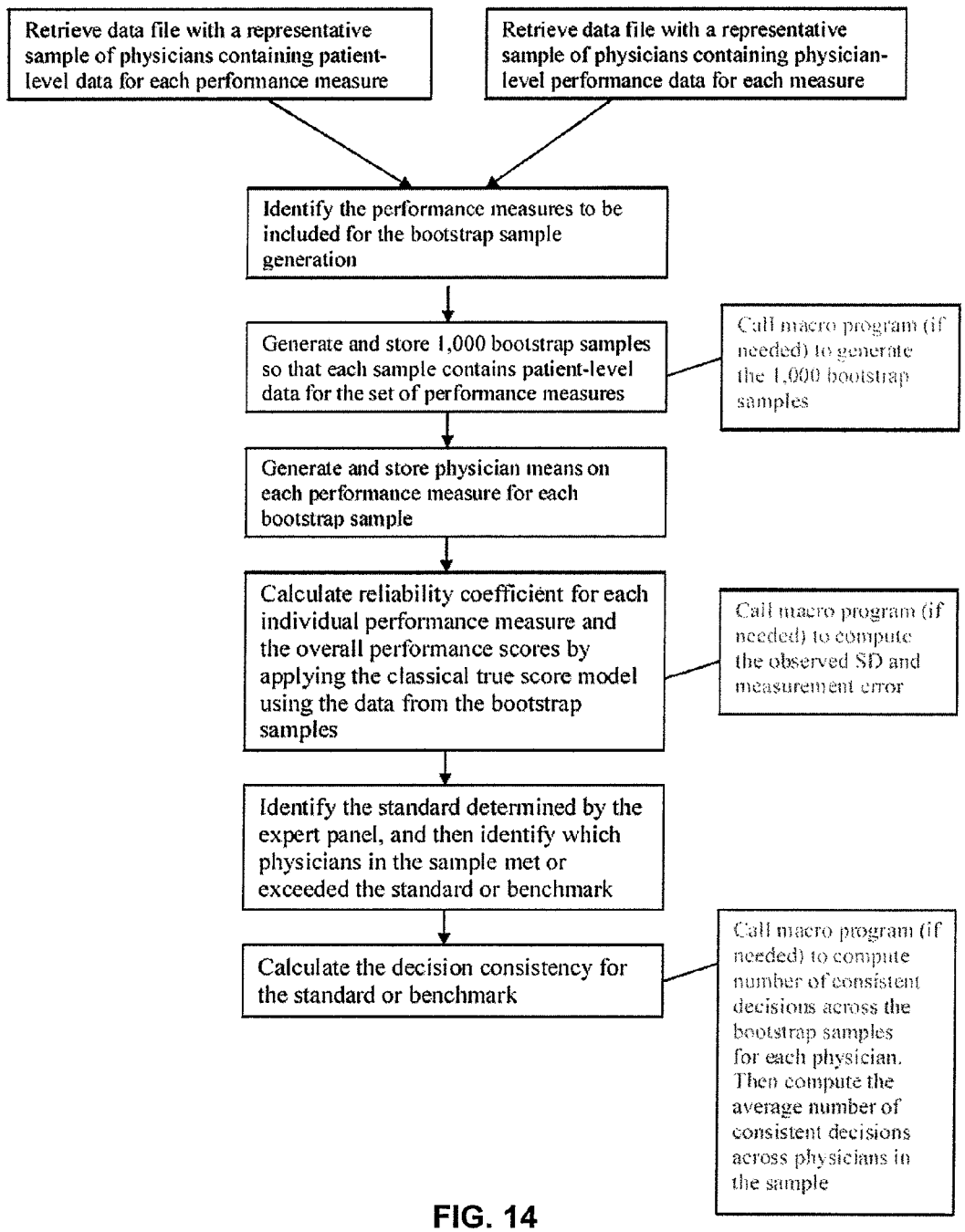
FIG. 14 illustrates an exemplary flowchart of the steps used in the two exemplary SAS® programs of FIGS. 12A, 12B and 13A-13J.

Because a physician's patient sample is frequently drawn from a larger panel of patients, the reliability of the overall performance scores should be evaluated, and the consistency of the resulting performance standard or benchmark should be estimated, as noted in step 230 of FIG. 2B. The reliability of each measure and for the overall performance scores can be estimated using, for example, measurement theory's classical true score model, $\sigma^2_{Observed} = \sigma^2_{True} + \sigma^2_{Error}$ (as described in Reeves D, Campbell S M, Adams J, et al. Combining multiple indicators of clinical quality: An evaluation of different analytical approaches. *Med Care.* 2007; 45:489-496, which is incorporated herein by reference, and is known to one of ordinary skill in the art). This method can be used for different types of measures and calculations (e.g., linear or non-linear, averages or all-or-none scoring). Specifically, 1,000 bootstrap samples can be obtained to estimate the standard error. The patient sample size is one factor that influences the reliability; the greater the size of the sample the higher the reliability and the lower the errors of measurement. FIGS. 12A and 12B present an exemplary SAS® program for generating the bootstrap samples and FIGS. 13A-13J present an exemplary SAS® program for estimating reliability of the individual measures and overall performance scores, as well as for estimating the decision consistency of the standard or benchmark. An exemplary flowchart of the steps used in the two exemplary SAS® programs of FIGS. 12A, 12B and 13A-13J is shown in FIG. 14. For the diabetes care example, the overall performance score reliability is calculated based on the reliabilities of the intermediate outcome and process measure composite scores, and from the patient experience measure scores using Mosier's formula (Mosier C I. On the reliability of a weighted composite. Psychometrika. 1943; 8:161-168, incorporated herein by reference and as known to one of ordinary skill in the art). A measure of decision consistency is also obtained using the same bootstrap procedure to determine the consistency of decisions over many different samples of patients. The procedure used to estimate reliability of the composite score is applied to each bootstrap replication, and the decisions are then compared to the original sample. The proportion of consistent decisions over all replications for each physician is calculated. These proportions were then averaged across physicians to form a decision consistency index. For example, the decision consistency index for the hypothetical standard of 48.19 presented herein was 0.98, that is with repeated sampling the same classification result (i.e., met borderline performance vs. did not meet borderline performance) would result 98% of the time.

The system has been described above as comprised of units. One skilled in the art will appreciate that this is a functional description and that the respective functions can be performed by software, hardware, or a combination of software and hardware. A unit can be software, hardware, or a combination of software and hardware. The units can comprise the physician quality software 106, wherein the physician quality software can comprise components to determine point values (or weights) for each of one or more performance measures and to rate one or a sample of physicians by applying the performance measures to the physician quality data 107 as described herein, as illustrated in FIG. 15 and described below. In one exemplary aspect, the units can comprise a computer 101 as illustrated in FIG. 15 and described below.

FIG. 15 is a block diagram illustrating an exemplary operating environment for performing the disclosed methods. This exemplary operating environment is only an example of an operating environment and is not intended to suggest any limitation as to the scope of use or functionality of operating environment architecture. Neither should the operating environment be interpreted as having any dependency or requirement relating to any one or combination of components illustrated in the exemplary operating environment.

The present methods and systems can be operational with numerous other general purpose or special purpose computing system environments or configurations. Examples of well known computing systems, environments, and/or configurations that can be suitable for use with the systems and methods comprise, but are not limited to, personal computers, server computers, laptop devices, and multiprocessor systems. Additional examples comprise set top boxes, programmable consumer electronics, network PCs, minicomputers, mainframe computers, distributed computing environments that comprise any of the above systems or devices, and the like.

The processing of the disclosed methods and systems can be performed by software components. The disclosed systems and methods can be described in the general context of computer-executable instructions, such as program modules, being executed by one or more computers or other devices. Generally, program modules comprise computer code, routines, programs, objects, components, data structures, etc. that perform particular tasks or implement particular abstract data types. The disclosed methods can also be practiced in grid-based and distributed computing environments where tasks are performed by remote processing devices that are linked through a communications network. In a distributed computing environment, program modules can be located in both local and remote computer storage media including memory storage devices.

Further, one skilled in the art will appreciate that the systems and methods disclosed herein can be implemented via a general-purpose computing device in the form of a computer 101. The components of the computer 101 can comprise, but are not limited to, one or more processors or processing units 103, a system memory 112, and a system bus 113 that couples various system components including the processor 103 to the system memory 112. In the case of multiple processing units 103, the system can utilize parallel computing.

The system bus 113 represents one or more of several possible types of bus structures, including a memory bus or memory controller, a peripheral bus, an accelerated graphics port, and a processor or local bus using any of a variety of bus architectures. By way of example, such architectures can comprise an Industry Standard Architecture (ISA) bus, a Micro Channel Architecture (MCA) bus, an Enhanced ISA (EISA) bus, a Video Electronics Standards Association (VESA) local bus, an Accelerated Graphics Port (AGP) bus, and a Peripheral Component Interconnects (PCI), a PCI-Express bus, a Personal Computer Memory Card Industry Association (PCMCIA), Universal Serial Bus (USB) and the like. The bus 113, and all buses specified in this description can also be implemented over a wired or wireless network connection and each of the subsystems, including the processor 103, a mass storage device 104, an operating system 105, physician quality software 106, physician quality data 107, which can include but is not limited to the performance measures, patient-level data for each performance measure, physician-level data for each performance measure, criteria and point values (or weight) for each performance measure, and overall performance standard (or cutscore); a network adapter 108, system memory 112, an Input/Output Interface 110, a display adapter 109, a display device 111, and a human machine interface 102, can be contained within one or more remote computing devices 114a,b,c at physically separate locations, connected through buses of this form, in effect implementing a fully distributed system.

The computer 101 typically comprises a variety of computer readable media. Exemplary readable media can be any available media that is accessible by the computer 101 and comprises, for example and not meant to be limiting, both volatile and non-volatile media, removable and non-removable media. The system memory 112 comprises computer readable media in the form of volatile memory, such as random access memory (RAM), and/or non-volatile memory, such as read only memory (ROM). The system memory 112 typically contains data such as physician quality data 107 and/or program modules such as operating system 105 and physician quality software 106 that are immediately accessible to and/or are presently operated on by the processing unit 103.

In another aspect, the computer 101 can also comprise other removable/non-removable, volatile/non-volatile computer storage media. By way of example, FIG. 15 illustrates a mass storage device 104 which can provide non-volatile storage of computer code, computer readable instructions, data structures, program modules, and other data for the computer 101. For example and not meant to be limiting, a mass storage device 104 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Optionally, any number of program modules can be stored on the mass storage device 104, including by way of example, an operating system 105 and physician quality software 106. Each of the operating system 105 and physician quality software 106 (or some combination thereof) can comprise elements of the programming and the physician quality software 106. Physician quality data 107 can also be stored on the mass storage device 104. Physician quality data 107 can be stored in any of one or more databases known in the art. Examples of such databases comprise, DB2®, Microsoft® Access, Microsoft® SQL Server, Oracle®, mySQL, PostgreSQL, and the like. The databases can be centralized or distributed across multiple systems.

In another aspect, the user can enter commands and information into the computer 101 via an input device (not shown). Examples of such input devices comprise, but are not limited to, a keyboard, pointing device (e.g., a "mouse"), a microphone, a joystick, a scanner, tactile input devices such as gloves, and other body coverings, and the like These and other input devices can be connected to the processing unit 103 via a human machine interface 102 that is coupled to the system bus 113, but can be connected by other interface and bus structures, such as a parallel port, game port, an IEEE 1394 Port (also known as a Firewire port), a serial port, or a universal serial bus (USB).

In yet another aspect, a display device 111 can also be connected to the system bus 113 via an interface, such as a display adapter 109. It is contemplated that the computer 101 can have more than one display adapter 109 and the computer 101 can have more than one display device 111. For example, a display device can be a monitor, an LCD (Liquid Crystal Display), or a projector. In addition to the display device 111, other output peripheral devices can comprise components such as speakers (not shown) and a printer (not shown) which can be connected to the computer 101 via Input/Output Interface 110. Any step and/or result of the methods can be output in any form to an output device. Such output can be any form of visual representation, including, but not limited to, textual, graphical, animation, audio, tactile, and the like.

The computer 101 can operate in a networked environment using logical connections through a network 115 to one or more remote computing devices 114a,b,c. By way of example, a remote computing device can be a personal computer, portable computer, a server, a router, a network computer, a peer device or other common network node, and so on. Logical connections between the computer 101 and a remote computing device 114a,b,c can be made via a local area network (LAN) and a general wide area network (WAN). Such network connections can be through a network adapter 108. A network adapter 108 can be implemented in both wired and wireless environments. Such networking environments are conventional and commonplace in offices, enterprise-wide computer networks, intranets, and the Internet.

For purposes of illustration, application programs and other executable program components such as the operating system 105 are illustrated herein as discrete blocks, although it is recognized that such programs and components reside at various times in different storage components of the computing device 101, and are executed by the data processor(s) of the computer. An implementation of physician quality software 106 can be stored on or transmitted across some form of computer readable media. Any of the disclosed methods can be performed by computer readable instructions embodied on computer readable media. Computer readable media can be any available media that can be accessed by a computer. By way of example and not meant to be limiting, computer readable media can comprise "computer storage media" and "communications media." "Computer storage media" comprise volatile and non-volatile, removable and non-removable media implemented in any methods or technology for storage of information such as computer readable instructions, data structures, program modules, or other data. Exemplary computer storage media comprises, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

The methods and systems can employ Artificial Intelligence techniques such as machine learning and iterative learning. Examples of such techniques include, but are not limited to, expert systems, case based reasoning, Bayesian networks, behavior based AI, neural networks, fuzzy systems, evolutionary computation (e.g. genetic algorithms), swarm intelligence (e.g. ant algorithms), and hybrid intelligent systems (e.g. Expert inference rules generated through a neural network or production rules from statistical learning).

EXAMPLES

The examples described herein are put forth so as to provide those of ordinary skill in the art with a complete disclosure and description of how the compounds, compositions, articles, devices and/or methods claimed herein are made and evaluated, and are intended to be purely exemplary and are not intended to limit the scope of the methods and systems. Efforts have been made to ensure accuracy with respect to numbers (e.g., amounts, temperature, etc.), but some errors and deviations should be accounted for.

For example, the above embodiments of a systems, methods and computer program products are described using an example of diabetes care performance using hypothetical data. It is to be appreciated that this is just one example of an application of the described embodiments and the scope of the claimed invention is not limited to this example/embodiment. Other applications of the disclosed embodiments include, for example, care of patients with hypertension, cardiovascular disease, or asthma.

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

Throughout this application, various publications may be referenced. The disclosures of these publications in their entireties are hereby incorporated by reference into this application in order to more fully describe the state of the art to which the methods and systems pertain.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A computer-implemented method for determining an overall performance score for a physician comprising:
   determining, by a computer, performance criteria and point weights for a plurality of performance measures associated with the delivery of patient care in a particular clinical domain, the performance criteria comprising a minimum performance criterion for each respective performance measure, the plurality of performance measures comprising at least one clinical performance measure;
   determining, by the computer, an overall performance standard or benchmark using the performance criteria and point weights;
   receiving clinical performance data associated with the treatment of a plurality of patients by respective physicians of a plurality of physicians, the clinical performance data comprising data indicative of the performance of each physician of the plurality of physicians with respect to each clinical performance measure of the plurality of performance measures;

transforming, by the computer, the clinical performance data for a primary sample of patients into an overall performance score for a selected physician of the plurality of physicians using point weights associated with each performance measure;

determining, by the computer, a decision indicative of whether the selected physician meets the overall performance standard or benchmark for the primary sample of patients;

transforming, by the computer, the clinical performance data for a plurality of secondary samples of patients into an overall performance score for the selected physician for each secondary sample of patients using the point weights associated with each performance measure, wherein each secondary sample of patients is different than the primary sample of patients;

determining, by the computer, for each secondary sample of patients, a decision indicative of whether the selected physician meets the overall performance standard or benchmark for the secondary sample of patients; and estimating, by the computer, a decision consistency of the overall performance standard or benchmark, wherein the decision consistency is indicative of the proportion of decisions for the plurality of secondary samples of patients that correspond to the decision for the primary sample of patients; and presenting, by the computer, an output indicative of the estimated decision consistency of the overall performance standard or benchmark.

2. The method of claim 1, wherein the step of determining, by the computer, a decision indicative of whether the selected physician meets the overall performance standard or benchmark for the primary sample of patients comprises comparing the overall performance score of the selected physician for the primary sample of patients to the overall performance standard or benchmark, and wherein the step of determining, by the computer, for each secondary sample of patients, a decision indicative of whether the selected physician meets the overall performance standard or benchmark for the secondary sample of patients comprises comparing the overall performance score of the selected physician for the secondary sample of patients to the overall performance standard or benchmark.

3. The method of claim 1, wherein determining, by the computer, the overall performance standard or benchmark comprises utilizing an Angoff standard-setting methodology adapted to determine the overall performance standard or benchmark, wherein the adapted Angoff standard-setting methodology comprises, for each performance measure of the plurality of performance measures, determining the minimum performance criterion indicative of the minimum acceptable level of physician performance for a selected patient population.

4. The method of claim 1, wherein determining, by the computer, the overall performance standard or benchmark comprises multiplying the minimum performance criterion for each performance measure by its respective point weight and summing each result to yield the overall performance standard or benchmark.

5. The method of claim 3, wherein determining point weights for each performance measure comprises determining an importance ranking for each performance measure using a Dunn-Rankin scaling method that calculates weights for each performance measure which are transformed into the point weights for each performance measure.

6. The method of claim 1, wherein transforming the clinical performance data into an overall performance score for the selected physician using the point weights associated with each performance measure comprises transforming the clinical performance data into numerical quantities and multiplying the numerical quantities by their respective point weight and summing each result to yield the overall performance score for the selected physician.

7. The method of claim 1, further comprising estimating a reliability of the overall performance score of the selected physician for the primary sample of patients.

8. The method of claim 7, comprising using measurement theory's classical true score model, $\sigma^2_{Observed} = \sigma^2_{True} + \sigma^2_{Error}$, to estimate the reliability of the overall performance score of the selected physician for the primary sample of patients.

9. A system for determining an overall performance score for a physician comprising:

a memory; and a processor operably connected with the memory, wherein said processor is configured to;

determine performance criteria and point weights for a plurality of performance measures associated with the delivery of patient care in a particular clinical domain, the performance criteria comprising a minimum performance criterion for each respective performance measure, the plurality of performance measures comprising at least one clinical performance measure;

determine an overall performance standard or benchmark using the performance criteria and point weights;

receive clinical performance data associated with the treatment of a plurality of patients by respective physicians of a plurality of physicians, the clinical performance data comprising data indicative of the performance of each physician of the plurality of physicians with respect to each clinical performance measure of the plurality of performance measures;

transform the clinical performance data and for a primary sample of patients into an overall performance score for a selected physician of the plurality of physicians using the point weights associated with each performance measure;

determine a decision indicative of whether the selected physician meets the overall performance standard or benchmark for the primary sample of patients;

transform the clinical performance data for a plurality of secondary samples of patients into an overall performance score for the selected physician for each secondary sample of patients using the point weights associated with each performance measure, wherein each secondary sample of patients is different than the primary sample of patients;

determine, for each secondary sample of patients, a decision indicative of whether the selected physician meets the overall performance standard or benchmark for the secondary sample of patients;

estimate a decision consistency of the overall performance standard or benchmark, wherein the decision consistency is indicative of the proportion of decisions for the at least one secondary sample of patients that correspond to the decision for the primary sample of patients; and present an output indicative of the estimated decision consistency of the overall performance standard or benchmark.

10. The system of claim 9, wherein the processor is further configured to:
compare the overall performance score of the selected physician for the primary sample of patients to the overall performance standard or benchmark; and
compare, for each secondary sample of patients, the overall performance score of the selected physician for the secondary sample of patients to the overall performance standard or benchmark.

11. The system of claim 9, wherein the processor is configured to determine the overall performance standard or benchmark utilizing an adapted Angoff standard-setting methodology, wherein the adapted Angoff standard-setting methodology comprises, for each performance measure of the plurality of performance measures, determining the minimum performance criterion indicative of the minimum acceptable level of physician performance for a selected patient population.

12. The system of claim 9, wherein the processor is configured to determine the overall performance standard or benchmark by multiplying the minimum performance criterion for each performance measure by its respective point weight and summing each result to yield the overall performance standard or benchmark.

13. The system of claim 11, wherein the processor is configured to determine the point weights for each performance measure by determining an importance ranking for each performance measure using a Dunn-Rankin scaling method that calculates weights for each performance measure which are transformed into the point weights for each performance measure.

14. The system of claim 9, wherein the processor is configured to transform the clinical performance data into an overall performance score for the selected physician using the point weights associated with each performance measure by transforming the clinical performance data into numerical quantities and multiplying the numerical quantities by their respective point weight and summing each result to yield the overall performance score for the selected physician.

15. The system of claim 9, wherein the processor is configured to estimate a reliability of the overall performance score of the selected physician for the primary sample of patients.

16. The system of claim 15, wherein the processor is configured to use measurement theory's classical true score model, $\sigma^2_{Observed} = \sigma^2_{True} + \sigma^2_{Error}$, to estimate the reliability of the overall performance score for the primary sample of patients.

17. A computer program product comprising computer-executable code sections stored on one or more non-transitory computer-readable mediums, wherein said computer-executable code sections comprise:
a first section for determining performance criteria and point weights for a plurality of performance measures associated with the delivery of patient care in a particular clinical domain, the performance criteria comprising a minimum performance criterion for each respective performance measure, the plurality of performance measures comprising at least one clinical performance measure;
a second section for determining an overall performance standard or benchmark using the performance criteria and point weights;
a third section for receiving clinical performance data associated with the treatment of a plurality of patients by respective physicians of a plurality of physicians, the clinical performance data comprising data indicative of the performance of each physician of the plurality of physicians with respect to each clinical performance measure of the plurality of performance measures;
a fourth section for transforming the clinical performance data for a primary sample of patients into an overall performance score for a selected physician of the plurality of physicians using the point weights associated with each performance measure;
a fifth section for determining a decision indicative of whether the selected physician meets the overall performance standard or benchmark for the primary sample of patients;
a sixth section for transforming the clinical performance data for a plurality of secondary samples of patients into an overall performance score for the selected physician for each secondary sample of patients using the point weights associated with each performance measure, wherein each secondary sample of patients is different than the primary sample of patients;
a seventh section for determining, for each secondary sample of patients, a decision indicative of whether the selected physician meets the overall performance standard or benchmark for the secondary sample of patients;
an eighth section for estimating a decision consistency of the overall performance standard or benchmark, wherein the decision consistency is indicative of the proportion of decisions for the plurality of secondary samples of patients that correspond to the decision for the primary sample of patients; and
a ninth section for presenting an output indicative of the estimated decision consistency of the overall performance standard or benchmark.

18. The computer program product of claim 17, wherein determining the overall performance standard or benchmark comprises utilizing an adapted Angoff standard-setting methodology to determine the overall performance standard or benchmark, wherein the adapted Angoff standard-setting methodology comprises, for each performance measure of the plurality of performance measures, determining the minimum performance criterion indicative of the minimum acceptable level of physician performance for a selected patient population.

19. The computer program product of claim 17, wherein determining an overall performance standard or benchmark comprises multiplying the minimum performance criterion for each performance measure by its respective point weight and summing each result into the overall performance standard or benchmark.

20. The computer program product of claim 18, wherein determining point weights for each performance measure comprises determining an importance ranking for each performance measure using a Dunn-Rankin scaling method that calculates weights for each performance measure which are transformed into the point weights for each performance measure.

21. The computer program product of claim 17, wherein transforming the clinical performance data into a physician's overall performance score for the selected physician using the point weights associated with each performance measure comprises transforming the clinical performance data into numerical quantities and multiplying the numerical quantities by their respective point weight and summing each result to yield the overall performance score for the selected physician.

22. The computer program product of claim 17, further comprising a tenth section of computer-executable code configured to estimate a reliability of the overall performance score of the selected physician for the primary sample of patients.

23. The computer program product of claim 22, wherein the tenth section of computer-executable code uses measurement theory's classical true score model, $\sigma^2_{Observed} = \sigma^2_{True} + \sigma_{Error}$, to estimate the reliability of the overall performance score for the primary sample of patients.

24. The method of claim 3, wherein the selected patient population is selected from the group consisting of a population of patients having diabetes, a population of patients having hypertension, a population of patients having cardiovascular disease, and a population of patients having asthma.

25. The method of claim 1, wherein the primary sample of patients includes at least one patient that is not included in at least one of the secondary samples of patients.

26. The method of claim 1, wherein at least one of the secondary samples of patients includes a patient that is not included in the primary sample of patients.

27. The method of claim 1, wherein the step of transforming, by the computer, the clinical performance data for a primary sample of patients into an overall performance score for a selected physician comprises transforming the clinical performance data for a primary sample of patients for each respective physician of the plurality of physicians into an overall performance score for each respective physician, wherein the step of determining, by the computer, a decision indicative of whether the selected physician meets the overall performance standard or benchmark for the primary sample of patients comprises determining, for each respective physician of the plurality of physicians, a decision indicative of whether the physician meets the overall performance standard or benchmark for the primary sample of patients, wherein the step of transforming, by the computer, the clinical performance data for a plurality of secondary samples of patients into an overall performance score for the selected physician for each secondary sample of patients comprises transforming the clinical performance data for a plurality of secondary samples of patients into an overall performance score for each respective physician for each secondary sample of patients, wherein the step of determining, by the computer, for each secondary sample of patients, a decision indicative of whether the selected physician meets the overall performance standard or benchmark comprises determining, for each respective physician of the plurality of physicians, a decision indicative of whether the physician meets the overall performance standard or benchmark for the secondary sample of patients, wherein the step of estimating, by the computer, a decision consistency of the overall performance standard or benchmark comprises estimating the decision consistency of the overall performance standard or benchmark for each respective doctor and averaging the decision consistencies associated with the plurality of doctors to form a decision consistency index for the overall performance standard or benchmark, and wherein the step of presenting, by the computer, an output indicative of the estimated decision consistency of the overall performance standard or benchmark comprises presenting an output indicative of the decision consistency index for the overall performance standard or benchmark.

28. The method of claim 1, wherein the plurality of performance measures further comprise at least one patient measure, each patient measure of the at least one patient measure being selected from the group consisting of a patient satisfaction measure and a patient self-care measure, wherein the method further comprises receiving patient data associated with the treatment of the plurality of patients by respective physicians of the plurality of physicians, the patient data comprising data indicative of the performance of each physician of the plurality of physicians with respect to each patient measure of the plurality of performance measures, wherein the step of transforming, by the computer, the clinical performance data for the primary sample of patients into the overall performance score comprises transforming the clinical performance data and the patient data for the primary sample of patients into an overall performance score for the selected physician using the point weights associated with each performance measure, and wherein the step of transforming, by the computer, the clinical performance data for the plurality of secondary samples of patients into the overall performance score for each secondary sample comprises transforming the clinical performance data and the patient data for each secondary sample of patients into an overall performance score for the selected physician for each secondary sample of patients using the point weights associated with each performance measure.

* * * * *